(12) United States Patent
Xia et al.

(10) Patent No.: US 6,812,213 B2
(45) Date of Patent: Nov. 2, 2004

(54) STEROIDAL SAPOGENINS AND THEIR DERIVATIVES FOR TREATING ALZHEIMER'S DISEASE

(75) Inventors: Zongqin Xia, Shanghai (CN); Yaer Hu, Shanghai (CN); Ian Rubin, Leicester (GB); Jonathan Brostoff, London (GB); Brian Whittle, East Yorkshire (GB); Weijun Wang, Huntingdon (GB); Phil Gunning, Walden (GB)

(73) Assignee: Phytopharm, plc, Cambridgeshire (GB)

( * ) Notice: Subject to any disclaimer, the term of this patent is extended or adjusted under 35 U.S.C. 154(b) by 0 days.

(21) Appl. No.: 10/077,493

(22) Filed: Feb. 15, 2002

(65) Prior Publication Data

US 2002/0193317 A1 Dec. 19, 2002

Related U.S. Application Data

(63) Continuation of application No. 09/647,110, filed on Jan. 11, 2001, now abandoned.

(30) Foreign Application Priority Data

Mar. 26, 1998 (GB) ..................................... GB9806513.9
Mar. 8, 1999 (GB) ..................................... GB 9905275.5

(51) Int. Cl.⁷ .............................................. A61K 31/70
(52) U.S. Cl. ....................... 514/26; 424/195.1; 424/725
(58) Field of Search ............................ 424/195.1, 725; 514/26

(56) References Cited

U.S. PATENT DOCUMENTS

| | | | |
|---|---|---|---|
| 3,890,438 A | | 6/1975 | Cayen et al. |
| 4,680,289 A | | 7/1987 | Applezweig |
| 4,800,080 A | | 1/1989 | Grollier et al. |
| 5,017,562 A | | 5/1991 | Holmes et al. |
| 5,589,182 A | | 12/1996 | Tashiro et al. |
| 5,804,239 A | | 9/1998 | Wiersma |
| 6,258,386 B1 | * | 7/2001 | Xia et al. ................ 424/725 |
| 6,593,301 B1 | | 7/2003 | Ma et al. |

FOREIGN PATENT DOCUMENTS

| | | | |
|---|---|---|---|
| CN | 1096031 | | 12/1994 |
| DE | 4303214 | * | 8/1994 |
| EP | 1024146 | | 2/2000 |
| WO | WO99/16786 | * | 8/1999 |

OTHER PUBLICATIONS

Blunden et al, Paper entitled "steroidal Sapogenins from Leaves of Agaveae Species" (copyrighted 1999).*
Beiping Ma, Abstract titled "The Use of Steroidal Saponin Compounds to Prevent Senility, and Novel Steroid Saponin Compounds" (copyrighted 1999).*
Ningyu et al, Paper titled "Sarsasapogenin Mechanism in Treating Senile Dementia" (copyright 1998).*
Blunden, G., et al, "Steroidal Sapogenins from Leaves of Agaveae Species" (Abstract), Phytochemistry, 1978, vol. 17(11), pp. 1923–1926, Elsevier Science Ltd., Oxford, United Kingdom.
Martin, et al., Definition of "Alzheimer's disease," The Bantam Medical Dictionary, 2nd Edition, 1981, p. 15, Bantam Books, New York.
Schwartz, Rochelle, et al., "Presynaptic Nicotinic Cholinergic Receptors Labeled by [3H] Acetylcholine on Catecholamine and Seratonin Axons in Brain," Journal of Neurochemistry, 1984, pp. 1495–1498, vol. 42, No. 5, Raven Press, New York.
Yi, Ningyu, et al.,"The Mechanism of a Sapogenin From Anemarrhenae Asphodeloides Bge in the Treatment of Senile Dementia"; Proceedings of the 6th International Symp. of the International Isotope Society, Philadelphia, 1997, p. 103.
Yi, Ningyu, et al., "Sarsasapogenin: Mechanism in Treating Senile Dementia," (Paper 62) Proceedings of the 6th International Symp. of the International Isotope Society, Philadelphia, 1997.
Sramek, John J., et al., "A Bridging Study of LU–25–109 in Patients with Probable Alzheimer's Disease," Life Sciences, 1998, pp. 195–202, vol. 62, No. 3, Elsevier Science, Inc.
Ma, Beiping, et al., "The Use of Steroidal Saponin Compounds to Prevent Senility, and Novel Steroid Saponin Compounds," 1999.
Yi, Ningyu et al., "Extraction of .beta.–adnergic receptor– and M cholinergic receptor–regulating (.beta.,5.beta., 25s)–spirostan–3–o 1 from Anemarrhena Asphodeloides Bunge," 1999.

* cited by examiner

Primary Examiner—Elli Peselev
(74) Attorney, Agent, or Firm—Fulwider Patton Lee & Utecht, LLP

(57) ABSTRACT

The invention discloses the use of a number of saponins and sapogenins, notably those of steroidal structure, in the treatment of cognitive disfunction and similar conditions. Methods of treatment, and pharmaceutical compositions are also disclosed.

27 Claims, No Drawings

STEROIDAL SAPOGENINS AND THEIR DERIVATIVES FOR TREATING ALZHEIMER'S DISEASE

RELATED APPLICATIONS

This application is a continuation of U.S. patent application Ser. No. 09/647,110, filed Jan. 11, 2001, now abandoned.

The present invention relates to membrane-bound receptors and their function; to cognitive disfunction and allied conditions; to treatments therefor; and to compositions for use in such treatments. More particularly but not exclusively the invention is concerned with the treatment of conditions that are characterised by a deficiency in the number or function of membrane-bound receptors. In the following, the present invention will be described principally with reference to the treatment of Alzheimer's disease (AD) and senile dementia of the Alzheimer's type (SDAT), where deficiencies in a number of receptor types have been demonstrated. However, it is to be understood that the present invention relates generally to the treatment of conditions attributable to intrinsic pathological conditions and/or exposure to adverse environmental conditions these conditions being characterised by a deficiency in the number or function of membrane-bound receptors or a deficiency in transmission at the junctions between neurones or at the junctions of neurones and effector cells.

Conditions of the type mentioned above include Parkinson's disease, Lewi body dementia, postural hypotension, autism, chronic fatigue syndrome, Myasthenia Gravis, Lambert Eaton disease, diseases and problems associated with Gulf War Syndrome, occupational exposure to organophosphorus compounds and problems associated with ageing.

Alzheimer's disease (AD) and senile dementia of the Alzheimer's type (SDAT) are grave and growing problems in all societies where, because of an increase in life expectancy and control of adventitious disease, the demographic profile is increasingly extending towards a more aged population. Agents which can treat, or help in the management of, AD/SDAT are urgently required.

Age-associated memory impairment (AAMI) is a characteristic of older patients who, while being psychologically and physically normal, complain of memory loss. It is a poorly defined syndrome, but agents which are effective in treatment of AD/SDAT may also be of value in these patients.

Research into AD/SDAT is being carried out by traditional and conventional medical research methods and disciplines. In conventional medicine, there are several approaches to the treatment of AD/SDAT. It is known that the biochemical processes subserving memory in the cerebral cortex are (at least in part) cholinergically-mediated. Those skilled in the art will know that "cholinergically mediated" mechanisms may be directly attributable to acetylcholine acting on receptors, and these are direct effects. Other, clinically useful effects may also be caused by modulation of release of acetylcholine from pre-synaptic nerve endings or inhibition of enzymes that destroy acetylcholine. These modulating factors may be exerted through neurones where the mediator is non-cholinergic; these are referred to as indirect effects. Some attempts at treatment have focussed on the role of other mediators such as 5-hydroxytryptamine, which is a mediator in other areas of brain, such as the mid-brain nuclei. However, since fibres from these areas are projected forward into the cerebral cortex where the primary transmitter is acetylcholine, attention has focussed on the management of this mediator in the search for appropriate therapeutic agents.

Cholinergic strategies for the treatment of AD/SDAT have been directed at several points along the pathway of formation, synaptic release and removal of released acetylcholine.

One approach involves treatment with high doses of lecithin and other precursors of acetylcholine. This is of limited use in producing sustained improvements in cognitive performance.

Another approach involves the use of vegetable drugs such as Polygalae root extract, which has been shown to enhance choline-acetylcholine transferase (CAT) activity and nerve growth factor (NGF) secretion in brain. Oral administration of NGF has no effect on central nervous system neurons because it is a high molecular weight protein that cannot pass through the blood-brain barrier. However, agents which can pass through the blood-brain barrier and have a stimulating effect on NGF synthesis in the central nervous system have been proposed for the improvement of memory-related behaviour.

The results of a third clinical approach, which uses cholinesterase inhibitors such as tacrine hydrochloride, have been marginally more positive than the above. Substances obtained from plants used in Chinese and Western medicine, for example huperzine, galanthamine, and physostignine have all been shown to be of some—although limited—benefit in the treatment of AD/SDAT in clinical studies and also in laboratory models. All of these substances are inhibitors of acetylcholine esterase (AChE). In patients with AD/SDAT, there may be reduced synthesis of acetylcholine (ACh), reduced efficiency in release of ACh from presynaptic stores, and a decrease in the number or function of postsynaptic ($M_1$) receptors. Reductions in pre-synaptic $M_2$ receptors have also been shown. The beneficial effect of AChE inhibitors is attributed to enhancement of acetylcholine levels at synapses in brain by slowing down the destruction of released transmitter.

Compositions which modulate cholinergic function are known to affect memory and recall. For example, nicotine stimulates nicotinic acetylcholine receptors, and the short lived memory enhancing effects of cigarette smoking are thought to be due to the effect of nicotine. Scopolamine, an antagonist of acetylcholine, will produce amnesia and impaired cognitive function manifesting in psychomotor tests as a prolongation of simple reaction times, possibly as a result of impaired attention, and is used for this purpose as an adjunctive analgesic treatment. The amnesic effect of scopolamine can be antagonised by nicotine.

There are two families of nicotinic receptor subtypes ($\alpha$ and $\beta$), and each includes four subgroups which differ in ligand specificity. The role of nicotinic receptors in the CNS is not well understood at the molecular level. It is possible that agents binding to nicotinic receptors may modify the rate of turnover at muscarinic receptor sites in brain. Nicotinic receptors are ligand-gated ion channels, and their activation causes a rapid (millisecond) increase in cellular permeability to $Na^+$ and $Ca^{++}$, depolarisation and excitation.

Another class of cholinergic receptors can be stimulated by muscarine. Such muscarinic (M) receptors are G protein-coupled receptors. Responses of muscarinic receptors are slower; they may be excitatory or inhibitory. They are not necessarily linked to changes in ion permeability. Five types of muscarinic receptors have been detected by cholinergic receptor cloning, and are designated as $m_1$-$m_5$. Pharmacological effects are associated with four of the cloned receptors and they are designated as $M_1$-$M_4$ based on pharmacological specificity.

Using specific receptor proteins and monoclonal antibodies, it has been possible to further localise muscarinic receptors in brain as $m_1$ (postsynaptic) and $m_2$ (presynaptic). In heart, $M_2$ receptors are postsynaptic. Presynaptic muscarinic receptors are thought to be inhibitory, the binding of ACh to these receptors attenuating the release of further ACh to provide a negative feedback mechanism for Ach release. Selective $M_2$ receptor antagonists which are preferentially distributed to the brain may therefore be useful in treating Alzheimer's disease.

It is known that, in disease states such as AD/SDAT, there is general neuronal loss and deficits in cholinergic nerve function. It has been speculated that the high affinity nicotinic binding sites in the remaining cholinergic neurons might be converted to low affinity binding sites in treating such diseases, thereby sustaining transmitter release. By lowering the affinity of the nicotinic binding sites, a quick desensitising process is avoided.

Agonist activation at nicotinic receptors in brain has rapid onset and offset. A decreased affinity of the nicotinic receptors will reduce the desensitisation process. Schwarz R. D. et al (J. Neuro Chem 42, (1984), 1495–8) have shown that nicotine binding sites are presynaptically located on cholinergic (and also 5-hydroxytryptaminergic and catecholaminergic) axon terminals. A change in high affinity binding sites on AD/SDAT may also induce a change in the modulatory effect the nicotinic binding sites may have on other transmitter systems.

Presynaptic cholinergic mechanisms are also under inhibitory control by GABAergic neurons and this inhibition is thought to be intensified in AD/SDAT. Removal or reduction of this inhibition intensifies presynaptic cortical cholinergic activity and enhances cognitive processing.

The interactions of interneuronal fibres innervated by nicotine (reducing binding affinity), and dis-inhibition of GABAergic fibres both have a presynaptic locus.

This is a simplistic model of central transmission, but provides a framework for understanding the attempts which have been made to increase the effective concentration of acetylcholine in central synapses. This further illustrates the concept of direct and indirect action. There are disadvantages attaching to the three conventional therapeutic approaches to AD/SDAT treatment mentioned above: ACh precursor supplementation, agonist replacement and acetylcholine esterase inhibition. These treatments may result in a short-term increase in the availability of ACh which may activate feedback mechanisms resulting in the desensitisation of postsynaptic receptors. On theoretical grounds, long term benefits would not be predicted and when treatment is interrupted, any benefits in management of AD/SDAT and AAMI disappear and the condition may even be aggravated.

It has been shown that a compound with $M_1$ agonist and $M_2/M_3$ antagonist activity improved cognitive performance in SDAT patients (Sramak et al, Life Sciences vol. 2, No. 3, 195–202, 1997). However, this compound causes unacceptable cholinergic side effects, such as fatigue, diarrhoea and nausea.

A more radical approach to AD/SDAT and AAMI aims to increase the number of postsynaptic ($M_1$) receptors, in brain. It is known from Chinese Patent No. CN1096031A, that sarsasapogenin (SaG) can up-regulate $M_1$ cholinergic receptors and also down-regulate (i.e. move towards normal levels of) β-adrenergic receptors, the number of which may be pathologically-raised in AD/SDAT.

The inventors have found a number of saponins and sapogenins which exhibit the ability to regulate receptors. Thus, according to one aspect of the invention, there is provided the use of one or more of smilagenin, anzurogenin D, or an astragaloside in the manufacture of a medicament for the treatment of a condition characterised by a deficiency in postsynaptic membrane-bound receptor number or function.

Those skilled in the art will be aware of the relationship between saponins and their sapogenins, and that the desired effects of sapogenins can be exhibited in patients by administration of the corresponding saponins, or a mixture thereof. Hydrolysis of at least a proportion of saporin occurs in the gastrointestinal tract. The skilled man will also be aware of the epimerisation of certain sapogenins under conditions of acid hydrolysis.

Not all saponins and/or their aglycones are useful treatments for AD/SDAT and some, such as the saponins and sapogenins from digitalis, have potent inotropic actions on the myocardium. This group of saponins does not appear to have effects on the central nervous system (CNS) which would predicate therapeutic use in AD/SDAT; their potency and toxicity at high doses also rule this out.

Some of the principal sapogemns are of the following general formula:

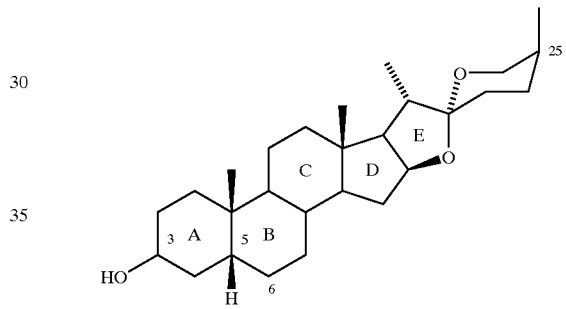

With reference to this general formula, the structure of certan sapogenins is as indicated in the Table below:

| Compound | A/B ring Cis/Trans/ unsaturation | C25 methyl stereochemistry (R or S) | Hydroxyl group(s) on Spirostane ring |
|---|---|---|---|
| Sarasasapogenin | Cis | S | 3β-OH |
| Smilagenin | Cis | R | 3β-OH |
| Anzurogenin-D | Trans | R | 3β-OH, 5α-OH, 6β-OH |
| Sisalgenin | Trans | S | 3β-OH (C═O at C12) |
| Tigogenin | Trans | R | 3β-OH |
| Diosgenin | Δ5 | R | 3β-OH |
| Ruscogenin | Δ5 | R | 1β-OH, 3β-OH |

The variation in pharmacological properties and pharmacodynamic actions of various types of sapogenin underlines the need for selection of those agents which are most useful for the treatment of AD/SDAT. The discovery of novel facts about the action of SaG has made it possible to determine which substances are most useful for the treatment of AD/SDAT and the like.

The saponins and sapogenins of principal interest in certain aspects of the present invention occur naturally in a range of plant species, notably from the genera Smilax, Asparagus, Anemarrhena, Yucca and Agave. The species presently of greatest interest include *Smilax regelii* Kilip & Morton—commonly known as *Honduran sarsaparilla; Smilax aristolochiaefolia* Miller—commonly known as *Mexican sarsaparilla*—Smilax ornata Hooker—commonly known as *Jamaican sarsaparilla; Smilax aspera*—commonly known as Spanish sarsaparilla; Smilax glabra Roxburgh; *Smilax febrifuga*—Kunth—commonly known as Ecuadorian or *Peruvian sarsaparilla; Anemarrhena asphodeloides* Bunge; *Yucca schidigera* Roezl ex Ortges; and Yucca brevifolia Enulm. Saponins and sapogenins which may be of interest also occur naturally in other genera, for example Dioscorea, Trillium, Solanum, Strophanthus, Digitalis and Trigonella. As indicated above, some saponins and sapogenins from these sources possess undesirable properties and are thus not recommended for use in the invention.

According to a further aspect of the present invention, there is provided a pharmaceutical composition having cognitive function enhancing properties which comprises an effective amount of a saponin or sapogenin. The saponin or sapogenin is preferably a steroidal saponin or sapogenin. Such a composition preferably comprises an effective amount of a non-oestrogenic saponin or sapogenin.

In another aspect, the invention provides a pharmaceutical composition having cognitive function enhancing properties which comprises an effective amount of a saponin or sapogenin (preferably a non-oestrogemic saponin or sapogenin) derived from a plant of the genus Smilax, Asparagus, Anemarrhenia, Yucca or Agave.

The invention further provides the use of an extract of a plant of the genus Smilax, Asparagus, Anemarrhena, Yucca or Agave in the preparation of a medicament having cognitive function enhancing properties.

It will be appreciated that the invention embraces within its scope the use of the compositions defined above. Thus, according to a fifth aspect, the present invention provides a method of enhancing cognitive function which comprises administering to a human or animal an effective dosage of a composition of the invention. The active aaent or agents may, for example, be administered in a food product or beverage.

The invention also provides a method of enhancing cognitive function in a human or non-human animal, which comprises administering an effective dose of a saponin or sapogenin, preferably a non-oestrogenic saponin or sapogenin.

As used herein, the term "cognitive function" refers to functions such as thinking, reasoning, remembering, imagining and learning.

Thus, according to a seventh aspect of the invention, there is provided the use of one or more of smilagenin, prazerigenin, an astragaloside, tigogenin, ruscogenin, hecogenin and diosgenin in the manufacture of a medicament for the treatment of a condition characterised by a deficiency in postsynaptic membrane-bound receptor number or function.

The inventors have also found that when sarsasapogenin is combined with certain other sapogenins, an unexpected synergistic effect is obtained.

Thus, according to an eighth aspect of the invention, there is provided a composition for the treatment of a condition characterised by a deficiency in postsynaptic membrane-bound receptor number or function, the composition comprising at least two of sarsasapogenin, smilagenin, prazerigenin, an astragaloside, tigogenin, ruscogenin, hecogenin and diosgenin.

The substances used in the seventh and eighth aspects of the invention do not have high overt oestrogenic and/or androgenic and/or anabolic activity in patients.

Nevertheless, in some embodiments, there is a low level of oestrogenic and/or androgenic supplementation.

According to a ninth aspect of the present invention, there is provided a method for the treatment of a condition which is characterised by a deficiency in membrane-bound receptor number or function in a tissue, organ, cell type or organelle, the method comprising:

modulating, directly or indirectly, the action of a cytosolic, nuclear or membrane-bound protein or receptor which, when it is activated by an agonist binding thereto, or when its activity is promoted by deactivation of an antagonist thereto, upregulates and/or normalises the number and/or turnover of membrane-bound receptors in that tissue, organ, cell type or organelle.

Surprisingly, the inventors have found that radiolabelled SaG is concentrated in the nuclei of brain cells isolated from rats, and that levels of M receptor mRNA are raised in rats treated with SaG. Whilst the inventors do not wish to be bound by any theory, it is believed that SaG exerts the effects described in Chinese Patent No. CN1096031A by modulating DNA expression.

One possible explanation in accordance with this invention is that SaG is an intracellular agonist of a steroid receptor, possibly the oestrogen receptor, or a transcription factor or promoter. There are chemical similarities in the structure of steroids and SaG, and it is therefore possible that the transport mechanism of SaG from cytoplasm to the nucleus is the same as that for steroids. Thus, after diffusing across the cell membrane, SaG binds to a steroid receptor present in the cytoplasm and promotes a conformational transformation of the receptor so that a high-affinity nuclear complex is delivered to a response site on the nuclear DNA protein complex. There, it enhances transcription of mRNA which migrates from the nucleus to the ribosomes to result in increased production of muscarinic receptors.

A second possibility is that SaG is an agonist of an unknown receptor, which acts to cause an increase in mRNA expression by binding to the DNA protein complex in the nucleus and acting as a promoter.

In either case, the binding of the SaG-receptor complex to DNA may cause an increase in the expression of mRNA which codes for cholinergic receptors, dopaminergic receptors, or adrenergic receptors or other membrane-bound receptors.

Alternatively, the binding of the SaG receptor complex to the DNA may cause an increase in the production of linked proteins such as G protein; or impede their degradation; or later the linkage between such proteins and associated receptors, thereby causing secondary changes in receptor number.

The effects of SaG may be mediated through increases in the levels of one or more neurotrophic factors, for example nerve growth factor (NGF).

It is also recognised that, in addition to the neuronal and cholinergically mediated synaptic mechanisms, it is possible that substances such as nitric oxide (NO) and non-cholinergic agonists can have a modulating effect on cholinergic transmission.

Whatever the precise nature of the cell component to which SaG binds in order to exert its effect, this provides a new pathway on which potential treatments for AD/SDAT, AAMI and the like can be targeted.

It has been shown that SaG increases the levels of membrane-bound receptor mRNA, specifically m, receptor mRNA. It is therefore possible that the cytosolic or nuclear receptor or promoter, when activated, increases the production of mRNA molecules in the tissue, organ, cell type or organelle which code for membrane-bound receptors, or that it decreases the breakdown of mRNA molecules in the tissue, organ, cell type or organelle which code for membrane-bound receptors.

The cytosolic or nuclear receptor, when activated, may also increase the transcription of mRNA molecules in the tissue, organ, cell type or organelle which code for membrane-bound receptors.

As mentioned above, nicotinic receptors may modulate the number and/or turnover of membrane-bound receptors. Accordingly, in one embodiment, the action of the cytosolic or nuclear receptor is modulated by administering a substance which is at least a partial agonist of nicotinic receptors.

It is presently preferred that the action of the cytosolic or nuclear receptor is modulated by administering a substance which is at least a partial agonist thereof.

The agonist may be a saponin or a sapogenin, preferably one or more of sarsasapogenin, smilagenin, prazerigenin, an astragaloside, tigogenin, ruscogenin, hecogenin and diosgenin. These compounds do not have a high overt oestrogenic and/or androgenic and/or anabolic activity in patients. A low level of oestrogenic and/or androgenic supplementation may be beneficial in the method of the ninth aspect of the present invention.

The receptor may be located in the cytosol of the cells of the tissue, organ, cell type or organelle and, when activated by binding an agonist, migrates to the nucleus of the cells. It is also possible that the receptor is located in the nucleus of the cells of the tissue, organ, cell type or organelle, the agonist diffusing into the nucleus or being transported there by another mechanism.

In the method in accordance with the first aspect of the present invention, it is not essential for an administered substance to act directly on the cytosolic or nuclear receptor itself. Instead, action can be taken either upstream or downstream of the cytosolic or nuclear receptors or promoters involvement in the pathway. Thus, the action of the cytosolic or nuclear receptor may be modulated by administering a substance which increases expression of the mRNA molecules in the tissue, organ, cell type or organelle which code for membrane-bound receptors.

The role of oestrogen and other related compounds as possible treatments for SDAT has received considerable interest. In the studies conducted to look at the effects of a cholinesterase inhibitor, tacrine, on cognitive function in patients with SDAT a secondary analysis suggested that all of the improvement was seen in female patients who were also receiving hormone (oestrogen) replacement therapy (ERT). Epidemiological data also suggest that ERT may protect against the development of SDAT. There is extensive work in the rat that suggests that ovariectomy results in reduced cognitive function and this effect can be reversed at least in part by the administration of oestrogen. The effects of oestrogen in this model may be to increase high affinity choline uptake in certain areas in the brain, particularly the hippocampus, thereby improving cholinergic transmission. In the same model, administration of oestrogen has been shown to increase the levels of mRNA for brain derived neurotropic factor (BDNF) using suitable in-situ hybridisation techniques (Singh 1995).

Possible mechanisms behind the effects of oestrogen have been investigated in in-vitro experiments. These studies have been undertaken using a neuroblastoma cell line and the response of the cells to serum deprivation or the effects of beta amyloid (BA) fractions. This latter stimulus is thought to be of particular relevance because of the prominence of amyloid plaques in the late stages of SDAT. Both serum deprivation and BA induce cell death. 17-β oestradiol has been shown to protect against cell death induced by serum deprivation and BA. The protective effect was not abolished when the 17-β oestradiol was tested in the presence of the oestrogen antagonist, tamoxifen. The non-oestrogenic enantiomer, 17-α oestradiol, was as effective in inhibiting cell death. Subsequent work has suggested that the protective effects of these compounds depends on the presence of a fully de-saturated phenolic A ring and an unblocked hydroxyl group at the three position (Simpkins 1997; Green 1997). In neuroblastoma cell cultures, oestrogenic compounds were shown to increase the release of nerve growth factor. The relevance of these findings to the effects of oestrogen in SDAT remains unclear.

Patent applications have been published which claim the usefulness of a number of steroid sapogenins having spirostane, furo-spirostane, spirosolane or solanidine structures in the treatment of diseases including SDAT. Two patent publications are of particular relevance here: Chinese patent publication No. CN1096031A discloses two-way regulatory effects of the spirostane sapogenin, sarsasapogenin, on β-adrenergic and M-cholinergic receptors. The disclosure in this document, however, is brief. The other document of relevance is patent publication DE 4303214A1 which claims the use of a very wide range of saponins and sapogenins in the treatment of a whole range of diseases that the inventors consider to be of viral origin. This disclosure is however of dubious value in that it is well recognised that there is no infective element to a very large number of the conditions that are characterised by deficient synaptic transmission and thus the basic premise of the alleged invention is flawed. In addition they present no data of any kind that allows one skilled in the art to be able to select a preferred compound from the large number that are claimed.

In identifying compounds that would have use in the treatment of SDAT and other diseases characterised by reductions in receptor numbers or synaptic transmission, the inventors have given consideration to the need to identify compounds that would have the desired effect but would be devoid of any oestrogenic effects, as these would be unacceptable, particularly in male patients. A number of the compounds claimed to have activity in patent application DE 4303214A1 have marked oestrogenic activity and are therefore unacceptable. This data is summarised below in Table 1.

TABLE 1

Oestrogenic effects of steroid sapogenin compounds and selected triterpenoid

| Compound | Oestrogenic Activity |
| --- | --- |
| Diosgenin | Positive |
| Anzurogenin D | Negative |
| Ruscogenin | Positive |
| Sarsasapogenin | Negative |
| Tigogenin | Negative |
| Astragaloside | Negative |
| Smilagenin | Negative |

In addition these compounds were tested at other steroid receptors as it was considered that compounds that would be of clinical sue should have no effects at the other steroid receptors. None of the compounds was found to have any activity at any of the following receptors:

Progesterone

Glucocorticoid

Testosterone

Thus the compounds that were shown not to have activity at the oestrogen receptor were also inactive at the other important steroid receptors.

The selected compounds have also been tested for their activity in a number of in-vitro assays. The assays/ experiments that were considered of key importance in determining possible activity in the elevation of membrane bound receptor numbers were as follows:

1. Chinese hamster ovary (CHO) cells transfected with the a DNA fragment coding for a muscarinic receptor. The cell line used for the majority of the experiments was a cell line expressing the m2 receptor.
2. The effects of muscarinic receptor expression in cultured cell lines of neuronal origin were investigated.
3. Cultured cardiac muscle cells obtained from neonatal Sprague Dawley rats. The cardiac muscle cells express muscarinic receptors, typically m2. The level of these receptors falls on prolonged culture and the effects of compounds of interest in preventing the fall in receptor numbers was investigated.

The methods and the results of these experiments are now described in turn.

1 CHO cell line experiments

The effects of various compounds on the expression of m2 receptors on CHO cells transfected with DNA for the m2 receptor were investigated. Receptor numbers were assayed using tritiated QNB binding and subtracting non-specific binding. Compounds were dissolved in DMSO and DMSO was used as a control. Compounds were tested at a range of final concentrations. Compounds were also tested in the presence and absence of tamoxifen to try to distinguish an oestrogen receptor mediated mechanism. The results are summarised in the table 2 below.

TABLE 2

Effects of compounds on the expression of $m_2$ receptors on CHO cells

| Compound | Molar concentration of compound | Effect on receptor expression—given as % increase compared to control (negative values in brackets) |
|---|---|---|
| Sarsasapogenin | $10^{-5}$ | 34 |
|  | $10^{-6}$ | (14) |
| Anzurogenin D | $10^{-5}$ | 22 |
|  | $10^{-6}$ | (26) |
| Sisalgenin | $10^{-5}$ | NS |
|  | $10^{-6}$ | NS |
| Smilagenin | $10^{-5}$ | 57 |
|  | $10^{-6}$ | 18 |
| Diosgenin | $10^{-5}$ | NS |
|  | $10^{-6}$ | NS |
| Ruscogenin | $10^{-5}$ | (22) |
|  | $10^{-6}$ | NS |
| Tigogenin | $10^{-5}$ | NS |
|  | $10^{-6}$ | NS |

NS = No significant effect

Thus the experiments indicate that several of the compounds were able to increase the number of muscarinic receptors expressed on the surface of CHO cells cultured in-vitro. The effect was not antagonised by tamoxifen, indicating that the mechanism involved did not involve the oestrogen receptor. Unlike in the work published by Simpkin et al it was found that there was no need for an intact phenol A-ring. Equally a number of compounds that are steroid sapogenins were devoid of activity. Furthermore, additional experiments indicated that β-oestradiol had a similar effect in increasing receptor expression when administered at a concentration of $10^{-5}$M.

2 Effects of compounds on cell survival

Other in vitro assays have been used to distinguish between active and non-active compounds. In particular various neuroblastoma cell lines including SKN-SN and SH-SY5Y cells as well as phaechromoacytoma cell lines have been cultured in vitro in the presence of P-amyloid fragments or serum depletion. A number of techniques to demonstrate the effectiveness of the compounds in protecting the cultured cells were investigated. These techniques included Trypan blue exclusion, chemiluminescence and release of lactate dehydrogenase. Of most interest was the observation that incubation of cells, in particular PC12 cells, with β-amyloid reduced the number of muscarinic receptors measured using radio-labelled ligand binding techniques. This reduction in receptor numbers was found to be ameliorated by the active compounds.

3 Effects of compounds on cultured cardiac muscle cells.

Cardiac muscle cells were isolated from the ventricular muscle of neonatal Sprague Dawley rats using standard techniques. Cells were cultured in vitro and muscarinic receptor numbers expressed on cell surfaces membrane fragments after homogenisation of cells harvested at various time points were estimated using specific binding of tritiated QNB. Preliminary experiments demonstrated that the number of receptors expressed tended to decline after 10 days of culture. The experiments were therefore designed to investigate the effects of the various compounds in inhibiting this decline in receptor numbers.

The results of these experiments are summarised in Table 4:

TABLE 4

Effects of various compounds on muscarinic receptor expression on cultured cardiac muscle cells

| Compound | Concentration of compound causing a significant increase in number of receptors expressed on neonatal cardiac muscle after 10 days in vitro culture |
|---|---|
| Diosgenin | NS |
| Anzurogenin D | $10^{-6}$ M |
| Ruscogenin | NS |
| Sarsasapogenin | $10^{-5}$ M |
| Tigogenin | NS |
| Astragaloside | $10^{-5}$ M |
| Smilagenin | $10^{-6}$ M |

NS = No significant effect

Surprisingly the inventors have found that sapogenins are preferentially concentrated in the nuclei of cells cultured in vitro. This is surprising because, as discussed above, sarasasapogenin (SaG) and some other compounds which have been shown to increase the number of muscarinic receptors do not bind to known steroidal receptors. In addition, it is surprising that SaG is preferentially taken up into the nucleus because the effects of these compounds can be seen in in-vitro assay systems that express the muscarinic receptor but where the DNA for the receptor has been transfected into the cytoplasm and hence is not under the normal nuclear control mechanism.

SaG and the other compounds that have been tested and shown to up-regulate the levels of receptors, have all been shown not to bind directly to any of the major known classes of membrane bound receptor. Thus it can be postulated that the observed effects are probably not due to for instance an effect at the nicotinic receptor and a consequential increase in the number of muscarinic receptors. This explanation appears to be even less plausible (although it cannot be excluded) if one considers that certain of the compounds have also been shown by the inventors to increase the number of beta adrenergic receptors expressed on peripheral blood lymphocytes. Thus the mechanism would appear to be one which has a more general effect on the regulation of membrane bound receptors.

It is speculated here that the effect of the active compounds claimed in this patent may operate through an effect on G protein and that the effects on receptor numbers are secondary to an effect on G-protein. When a membrane bound G-protein linked receptor is stimulated two basic sets of events are initiated: the effecter response; and the internalisation of the receptor. The subsequent processing of the receptor to the state where it is again in a form on the cell surface or other membrane surface where it can interact with another receptor ligand appears to be subject to a number of factors. A number of these factors or mechanisms appear to be G-protein linked. There is evidence that activation of m, receptors may have an effect on G-protein expression or levels. It is speculated that the actions of the compounds described in this patent may due to an interaction in the processes of receptor regeneration, G-protein linkage or G-protein homeostasis.

An alternative hypothesis is that the compounds are increasing the synthesis or release or a decreased rate of degradation of neurotropic factors such as brain derived growth factor and/or nerve growth factor. These effects on growth factors might be due to an effect of the compound on a cytosolic or nuclear receptor or the binding of a compound to a promoter region with a consequent effect directly on the rate of production of mRNA for the growth factor or as a consequence of increasing the production of another material factor such as G-protein or finally the effects may be secondary to an effect on receptor or G-protein procession.

The increased expression and/or abnormal processing of the amyloid precursor protein (APP) is associated with the formation of amyloid plaques and cerebrovascular amyloid deposits which are the major morphological hallmarks of Alzheimer's disease. Of particular interest are the processes regulating the proteolytic cleavage of APP into amyloidogenic and nonamyloidogenic fragments. The cleavage of APP by the enzyme a-secretase within the β-amyloid sequence of the protein results in the formation of a non amyloidogenic C-Terminal fragment, and the soluble APPsa fragment; this latter fragment has been shown to have neurotropic and neuroprotective activity as well as to enhance memory in mice when injected intra-cerebro-ventrically (ICV). In contrast, processing of APP by β-secretase exposes the N-terminus of β-amyloid which is released by γ-secretase cleavage at the variable C-terminus. The resulting β-amyloid peptides, which contain 39–43 amino acids, have been shown to be neurotoxic and to accumulate in plaques which interfere with inter-neurone connections.

A number of studies have shown that stimulation of the protein-kinase (PKC) linked muscarinic $M_1$ and $M_3$ receptors results in an increase in α-secretase activity. As a consequence processing of APP to APPsa with its neuroprotective effects is increased. In parallel, processing of APP by β- and γ-secretase is decreased and there is a consequential reduction of β-amyloid. Other transmitters such as nerve growth factor (NGF) and brain derived neurotropic factor (BDNF) as well as bradykinin and vasopressin may have similar effects in increasing the proportion of APP processed to APPsa. There may be a number of factors involved in the effects of NGF which may include binding of the factor to the tyrosine kinase receptor (TrkA) and the stimulation of phospholipase Cγ with subsequent phosphorylation and activation of protein kinase C (PKC) and increase in relative activity of α-secretase.

Any treatment which increases activity of protein-kinase C selectively in brain might therefore be expected to be of use in the management of Alzheimer's disease. Until recently agonists selective at the $M_1$ receptor have not been available. Non-selective agonists would be expected to stimulate pre-synaptic $M_2$ receptors which cause negative feedback and hence would further severely impair muscarinic transmission. Selective agonists at the $M_1$ receptor are now becoming available (taisaclidine) and such agents are under investigation for the treatment of AD. There is however, a substantial risk that, as with the chronic administration of any receptor agonist, the clinical benefits seen will be severely limited in terms of the size of benefit by reducing receptor numbers or reducing sensitivity and in terms of side effects due to lack of receptor specificity. Thus compounds as described in this invention, which selectively increase muscarinic $M_1$ receptor numbers, with little or no effect on muscarinic $M_2$ receptor numbers in the brain would be expected to be devoid of the problems seen with a muscarinic agonist and hence have particular utility. Indeed the benefits may be seen in three parts as follows.

1. A selective increase in $M_1$ receptor numbers leading to increased synaptic transmission. Chronic administration of a selective agonist will at best, have no adverse effect on transmission;
2. Secondary to the increased receptor numbers, an increase stimulation of PKC with a consequential increase in a-secretase activity, leading to:
2.1 A reduced production of β-amyloid and a consequent reduction of plaque formation and neuronal loss;
2.2 An increase in APPsα and a consequent improvement in cerebral function as witnessed by an improvement in short and long term memory.

Finally the effects of the GABA system in modulating transmission has been discussed above. It is well know that there is a steroid binding site on the GABA receptor that is distinct from the benzodiazepine, chloride and GABA binding sites. A number of therapeutic compounds are know to bind to this site and have been used to enhance or reduce the level of consciousness. It is speculated that the chronic administration of a partial agonist at this site might lead to an enhancement of transmission.

The invention will be described further in the following example.

EXAMPLE

Investigation of mRNA Levels Using in Situ Hybridisation 20 months old pure-line male SD rats were divided randomly into 2 groups. One group received an average of 3 mg of sarsasapogenin per rat per day mixed into the daily feed. The control group received normal food and water. Four months later, their brains were used in hybridisation technique experiments, with 4 to 6 months old rats used as a young control group. Other feeding arrangements for each group were completely identical.

A cDNA chain which respectively corresponds to the maNA of both $m_1$ and $m_2$ was synthesised, $m_1$ corresponds to the 3–18 amino acid sequence of receptor protein, i.e. TGG TGC CAA GAC AGT GAT GTT GGG ACT GAC AGC AGG GGG CAC TGA GGT, and $M_2$ to the 1–16 amino acid sequence, i.e. ATG AAT AAC TCA ACA AAC TCC TCG AAC AAT GGC TTG GCT ATT ACC AGT. The cDNA was labelled using a 3'-terminal-label reagent kit with a-$^{35}$S-dATP (8.9 TBq/mmol) as the label material. After the reaction had finished, it was purified with a nucleotide column. The specific activity of the batch was estimated (16.67–33.34)×108 MBq/μg. a-$^{35}$S-dATP, 3'-terminal-label reagent kit and nucleotide column were obtained from Du Pont Co., USA.

One rat was obtained from each group each time and parallel experiments were performed. The rats were decapitated and their brains removed intact. 15 μm thick coronal slices were prepared in a constantly freezing cryo-microtome (AS-600 cryo-microtome, Anglia Scientific Co, UK). Slices were taken from different areas (identical places for each rat) and were mounted on slides smeared with polylysine, dried in a cool current of air, fixed in a solution of 4% paraformaldehyde (containing 1×phosphate buffer saline (PBS), pH 7.0) for 5 minutes before being washed twice in PBS. They were then placed in 0.25% acetic anhydride solution (containing 0.1 M triethanolamine hydrochloride, Ph 8.0, and 0.9% sodium chloride) for 10 minutes, dehydrated in 70%, 80%, 95%, and 100% ethyl alcohol for 1 minute, degreased in chloroform for 5 minutes, and finally treated in 100% and 95% ethyl alcohol for 1 minute successively.

Slices used as negative controls were taken and dehydrated in ethyl alcohol etc. as detailed above, but treated in advance in 100 mg $m_1$ RNase and 2×SSC solution (salt/sodium citrate solution containing 300 mmol/L sodium chloride and 45 mmol/L sodium citrate) for 2 hours at 37° C.

For hybridisation, the fluid matrix for hybridisation was compounded with freshly containing 50% deionised formamide, 4×SSC, 10% dextran sulphate, 250 μg/μl yeast tRNA, 5×Denhard solution, 500 μg/ml denaturation protamine DNA, 10 mmol/L dithiothreitol. Oligonucleotide probe [(16.67–33.34)×10 MBq/50 μl] labelled with $^{35}$S was added finally and mixed evenly. 50 μl of the matrix was dripped onto each slice and a silicate cover glass was placed lightly over, avoiding airlocks. The slices were then shelved in a hybridisation box with 2×SSC on the bottom to preserve moisture, and incubated at 37° C. for 18 to 24 hours.

After hybridisation, the slides were soaked in 1×SSC solution and shaken slightly to rinse the cover glass. They were washed in 1×SSC solution briefly, then vibrated gently in 2×SSC containing 50% formamide at 37° C. for 20 minutes with the solution changed four times, and then transferred into 1×SSC solution for vibration at laboratory temperature for 30 minutes (repeated twice). Finally, the slides were washed with double distilled water, dehydrated with 70%, then 95% ethyl alcohol and dried in the air.

Autoradiographs were prepared in a dark room, the specimen and the hyperfilm beta max being pressed together using the contact method and placed in a cassette with a desiccant, exposed at 4° C. for 2 to 3 weeks. They were developed (D196) and fixed (F5). Finally, the autoradiographs were analysed using a computerised image analyser (VIDAS imaging analyser, Kontron, Germany).

The $m_2$ probe failed to show any localised area of activity. The $m_1$ probe showed activity in dentate nucleus, cerebral cortex and striatum. Comparison of these three areas for the different animal groups are shown in Table 5:

TABLE 5

| Area | Comparison | |
|---|---|---|
| | Aged vs young | SaG vs Aged |
| Cortex | −5.14 ± 2.68 (23) | 5.77 ± 3.82 (20) |
| Hippocampus | −3.18 ± 2.87 (12) | 0.96 ± 4.26 (10) |
| Striatum | −12.2 ± 3.6* | 15.71 ± 3.27* (10) |

Positive means increased compared to the comparator.
*$p < 0.01$. Numbers in brackets = numbers of slices.

There was a significant reduction in mRNA expression for $m_1$ receptors in the striatum of aged rats compared to young controls. Administration of SaG resulted in a significant increase in $m_1$ receptor mRNA in the same brain area when treated animals were compared to aged, untreated controls.

What is claimed is:

1. A method of enhancing cognitive function in a human or non-human animal, which comprises administering to said animal an effective amount of one or more active agent selected from the group consisting of smilagenin and anzurogenin-D.

2. A method as claimed in claim 1, wherein at least two active agents are administered, selected from the group consisting of smilagenin, sarsasapogenin and anzurogenin-D.

3. A method as claimed in claim 1, wherein the active agent is smilagenin.

4. A method as claimed in claim 1, wherein the animal is a human suffering from Alzheimer's disease or senile dementia of the Alzheimer's type.

5. A method as claimed in claim 1, wherein the animal is a human suffering from Parkinson's disease.

6. A method as claimed in claim 1, wherein the animal is a human suffering from Lewi Body dementia.

7. A method as claimed in claim 1, wherein the animal is a human suffering from postural hypotension.

8. A method as claimed in claim 1, wherein the animal is a human suffering from autism.

9. A method as claimed in claim 1, wherein the animal is a human suffering from chronic fatigue syndrome.

10. A method as claimed in claim 1, wherein the animal is a human suffering from Myasthenia Gravis.

11. A method as claimed in claim 1, wherein the animal is a human suffering from Lambert Eaton disease.

12. A method as claimed in claim 1, wherein the animal is a human suffering from Gulf War Syndrome.

13. A method as claimed in claim 1, wherein the animal is a human suffering from occupational exposure to organophosphorus compounds.

14. A method as claimed in claim 1, wherein the animal is a human in old age.

15. A method as claimed in claim 2, wherein the animal is a human suffering from Alzheimer's disease or senile dementia of the Alzheimer's type.

16. A method as claimed in claim 2, wherein the animal is a human suffering from Parkinson's disease.

17. A method as claimed in claim 2, wherein the animal is a human suffering from Lewi Body dementia.

18. A method as claimed in claim 2, wherein the animal is a human suffering from postural hypotension.

19. A method as claimed in claim 2, wherein the animal is a human suffering from autism.

20. A method as claimed in claim 2, wherein the animal is a human suffering from chronic fatigue syndrome.

21. A method as claimed in claim 2, wherein the animal is a human suffering from Myasthenia Gravis.

22. A method as claimed in claim 2, wherein the animal is a human suffering from Lambert Eaton disease.

23. A method as claimed in claim 2, wherein the animal is a human suffering from Gulf War Syndrome.

24. A method as claimed in claim 2, wherein the animal is a human suffering from occupational exposure to organophosphorus compounds.

25. A method as claimed in claim 2, wherein the animal is a human in old age.

26. A method as claimed in claim 1, wherein the active agent is administered in a medicament.

27. A method as claimed in claim 2, wherein the active agents are administered in a medicament.

* * * * *

UNITED STATES PATENT AND TRADEMARK OFFICE
CERTIFICATE OF CORRECTION

| | |
|---|---|
| PATENT NO. | : 6,812,213 B2 |
| DATED | : November 2, 2004 |
| INVENTOR(S) | : Zongqin Xia et al. |

It is certified that error appears in the above-identified patent and that said Letters Patent is hereby corrected as shown below:

Title page,
Item [63], Related U.S. Application Data, please amend to read:
-- Continuation of application No. 09/647,110, filed Jan. 11, 2001, now abandoned, which was the US Nation Phase application corresponding to PCT application No. PCT/GB99/00951, which wase filed on March 26, 1999. --.

Column 1,
Lines 6-8, under "RELATED APPLICATIONS", please amend to read:
-- This application is a continuation of U.S. patent application Ser. No. 09/647,110, filed Jan. 11, 2001, now abandoned which was the US National Phase application corresponding to PCT application No. PCT/GB99/00951, which was filed on March 26, 1999. --.

Signed and Sealed this

Eleventh Day of October, 2005

JON W. DUDAS
*Director of the United States Patent and Trademark Office*

```
                           SEQUENCE LISTING

<160> NUMBER OF SEQ ID NOS: 2

<210> SEQ ID NO 1
<211> LENGTH: 48
<212> TYPE: DNA
<213> ORGANISM: Rat M1

<400> SEQUENCE: 1
tggtgccaag acagtgatgt tgggactgac agcaggggc actgaggt           48

<210> SEQ ID NO 2
<211> LENGTH: 48
<212> TYPE: DNA
<213> ORGANISM: Rat M2

<400> SEQUENCE: 2
atgaataact caacaaactc ctcgaacaat ggcttggcta ttaccagt          48
```